United States Patent [19]
Guy et al.

[11] 4,025,613
[45] May 24, 1977

[54] TIMED-RELEASE ASPIRIN

[75] Inventors: Michael G. Guy, Ferdonia; Richard G. Powers, Saukville, both of Wis.

[73] Assignees: Richard G. Powers, Saukville; Michael G. Guy, Ferdonia; James F. Stern; Robert M. Stern, both of Milwaukee, all of Wis.

[22] Filed: June 25, 1975

[21] Appl. No.: 590,095

Related U.S. Application Data

[60] Division of Ser. No. 435,418, Jan. 22, 1974, Pat. No. 3,906,086, which is a continuation of Ser. No. 163,739, July 19, 1971, abandoned.

[52] U.S. Cl. .............................. 424/21; 264/113; 264/115; 264/122
[51] Int. Cl.² ........................................ D04H 1/16

[58] Field of Search ............... 264/113, 122, 115; 424/21

[56] References Cited

UNITED STATES PATENTS

| | | | |
|---|---|---|---|
| 3,115,441 | 12/1963 | Hermelin | 424/22 |
| 3,488,418 | 1/1970 | Holliday et al. | 424/35 |

*Primary Examiner*—Robert F. White
*Assistant Examiner*—James R. Hall
*Attorney, Agent, or Firm*—Michael, Best & Friedrich

[57] ABSTRACT

A method for making multi-layer aspirin tablets including a timed-release layer by coating particles of standard aspirin prior to tabletting with an organic solvent solution containing cellulose acetate phthalate and a plasticizer and pressing together separate layers of the thus-coated aspirin and standard uncoated aspirin into a double-layer tablet.

7 Claims, 2 Drawing Figures

TIMED-RELEASE ASPIRIN

CROSS-REFERENCE TO RELATED APPLICATIONS

This application is a division of application Ser. No. 435,418 filed Jan. 22, 1974, which issued as U.S. Pat. No. 3,906,086 on Sept. 16, 1975, which in turn is a continuation of Ser. No. 163,739, filed July 19, 1971 abandoned.

BACKGROUND OF THE INVENTION

This invention relates to a method for making pharmaceutical preparations, and more particularly to pharmaceutical preparations having timed-released characteristics.

The maximum time of effectiveness in many pharmaceutical preparations, particularly those containing aspirin as the active analgesic agent, is only a few hours because of biological decomposition of the medication in the body. Consequently, repeated dosages must be taken at frequent intervals to obtain long term pain relief. Furthermore, aspirin usually dissolves readily in the gastric juices of the stomach and the total dosage is immediately fed into the blood stream. The level of the aspirin in the blood stream constantly decreases because of the biological decomposition, so there is little or no pain relief at the end of the period between dosages. As a result, the pain relief fluctuates between dosages corresponding to the peaks and valleys in the level of aspirin in the blood.

Many attempts have been made to devolop timed-released pharmaceutical preparations which provide a more constant level of aspirin in the blood over several hours. Generally, three different approaches have been employed to obtain a timed release. In one approach, employing digestion as the release mechanism, the aspirin is either coated or entrapped in a substance which is slowly digested or dispersed into the intestinal tract. The rate of availability of the aspirin is a function of the rate of digestion of the dispersible material. Therefore, the release rate, and thus the analgesic effectiveness of the aspirin, varies from patient to patient depending upon the ability of the patient to digest the material.

In another approach, such as disclosed in U.S. Pat. No. 3,247,066, the aspirin is dispersed in a water-soluble colloid and then coated with a rupturable plastic, non-digestable material which is permeable to the diffusion of water. After ingestion and upon entering the gastrointestinal tract, water in the body fluids diffuses through the coating and causes the colloid to swell. The coating is ruptured by the swelling colloid and the total content of aspirin is released. Although there is substantially less variation in the rate of release from patient to patient, substantially all of the aspirin is released at once resulting in an initially high blood level content which decreases rapidly with time. Also, the additional ingredients and processing steps to disperse the aspirin in the colloid and provide the coating substantially increases the cost of the product.

In another approach commonly referred to as microencapsulation, such as disclosed in U.S. Pat. Nos. 3,488,418, 3,341,416 and 3,155,590, particles of aspirin are first dispersed in a hot solution containing ethyl cellulose and a phase-separation inducing agent, such as butyl rubber or polyethylene. Upon cooling the aspirin particles become coated with ethyl cellulose. The coated particles are then admixed with tabletting excipients and formed into dosage-sized tablets. When ingested, the tablets disintegrate rapidly and the individual particles of encapsulated aspirin are dispersed in the stomach. The gastric juices slowly diffuse through the encapsulant walls, dissolve the aspirin, and the dissolved aspirin slowly diffuses or leaches out through the encapsulant walls into the body. Although the resultant blood level content remains more constant, the aspirin is diffused into the body rapidly enough so there is an initially high blood level content which decreases quite rapidly within a few hours, apparently because of the large surface area contact between the body fluids and the small encapsulated particles. Also, the cost of the additional ingredients and multiple processing steps add to the overall cost of the product.

U.S. Pat. No. 3,115,441 discloses another encapsulation method wherein particles of aspirin are first given a quick thin coating of a film-forming material and a non-toxic, hydrophobic material and are then coated with successive coatings of an organic solvent-resistant material. The coated particles are mixed with uncoated aspirin and this mixture is then formed into a tablet with the coated tablets being entrapped in a matrix of the uncoated aspirin. Tablets made according to this method have the advantage of providing immediate relief because the matrix material (which comprises the initial dosage) dissolves immediately upon ingestion. However, as with the other preparations employing the diffusion technique discussed above, the tablet rapidly disintegrates in the stomach and there is a relatively rapid release of the aspirin. Also, the several coating steps of the process add to the overall cost of the product. cl SUMMARY OF THE INVENTION The primary object of this invention is to provide a simple, inexpensive method for making a time-release pharmaceutical preparation containing aspirin as the active therapeutic agent which produces an improved blood level profile of the aspirin for prolonged durations.

Another object of this invention is to provide such a product which is also capable of providing immediate medication upon ingestion.

It has been found that aspirin tablets providing an improved blood level profile can be prepared by simply applying a film of a non-aqueous solution of cellulose acetate phthalate over either individual particles of aspirin before tabletting or over the outside of tablets formed from untreated aspirin particles, which upon drying forms a coating of cellulose acetate. When individual particles of aspirin are used, they are first coated with the solution, preferably during granulation, then, after drying, are formed into dosage-size tablets. The cellulose acetate phthalate is substantially insoluble in the acidic gastric juices of the stomach and the tablet remains in tact until it reaches the intestinal tract rather than disintegrating in the stomach and dispersing the individual aspirin particles. From in vitro and in vivo tests, it has been found that the aspirin is released in the intestinal tract at a slow, controlled rate as the cellulose acetate phthalate coating is eroded away by the alkaline intestinal fluids. The dissolution of the tablet as the coating erodes away appears to be somewhat analogous to that of a melting ice cube. Hence, the danger of damage from small particles lodging in a stomach or intestinal urevise associated with prior art timed-release pharmaceutical preparations is eliminated.

Because of the slow, controlled release rate of aspirin tablets prepared in accordance with this invention, a higher initial dosage can be taken without producing a high peak in the blood level content with potential toxicity and/or harmful side effects. Furthermore, by taking smaller dosages at regular intervals following the initial dose, the aspiring content in the blood can be maintained at a relatively constant pain relief level for periods of 24 hours or longer. This is a significant improvement over presently available timed-released aspirin which produce a blood level profile with substantial peaks and valleys between dosages and are ineffective within a few hours after ingestion.

In order to obtain both immediate and prolonged pain relief, a separate layer of uncoated aspirin particles can be tabletted with a layer of aspirin particles coated with cellulose acetate phthalate. The layer of uncoated particles dissolves in the stomach while the layer of coated particles remains in tact until reaching the intestinal tract where it dissolves at a slow, controlled rate.

The process of this invention basically is the same as that for making ordinary aspirin tablets, with the simple additional step of applying the coating solution to the aspirin particles before tabletting or to the outside of the tablet after it is formed. Hence, the cost for incorporating a timed-release characteristic is drastically reduced from that of prior art techniques requiring multiple and complex coating and/or matrixing steps, as well as costly coating ingredients. Also, all the ingredients of the cellulose acetate phthalate coating solution remining after drying are soluble in the body and are well known to be safe for human consumption. It has been found that timed-released aspirin prepared in accordance with this invention has excellent stability against hydrolysis and other chemical reactions. Hence, the aspirin has long term shelf life capabilities; a capability which many available timed-released preparations do not possess.

DESCRIPTION OF THE PREFERRED EMBODIMENT

Figure 1:
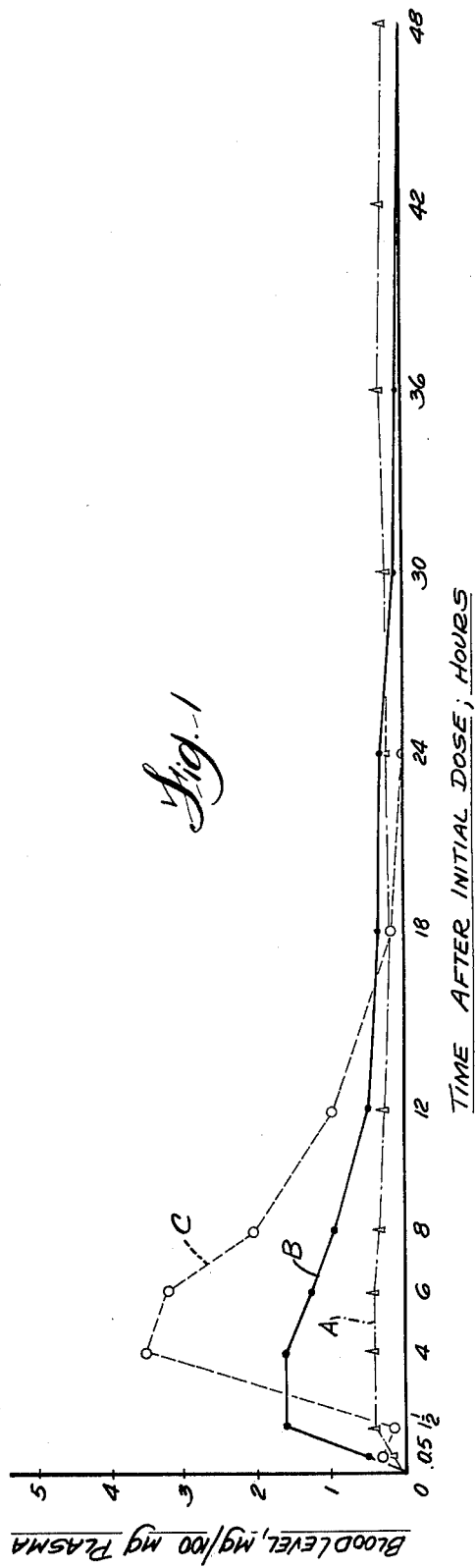
FIG. 1 is a graphical illustration of the results of the tests described in Example IV showing blood level profiles for aspirin made in accordance with this invention and a commercially available timed-released aspirin.

The coating solution used in this invention is made by dissolving cellulose acetate phthalate in a suitable non-aqueous, pharmaceutically acceptable (i.e., safe for human consumption) solvent. A wide variety of polar and non-polar organic solvents which are safe for human use and are capable of dissolving cellulose acetate phthalate are well known. Representative examples of such solvents include acetone, methyl ethyl ketone, methanol, ethanol, isopropanol, methylene chloride, ethylene dichloride, chloroform, and mixtures of these solvents. Presently the preferred solvent is a mixture of acetone and methylene chloride. It has been found that coating solutions containing concentrations of cellulose acetate phthalate over relatively broad ranges can be used to obtain the improved timed-released characteristics of this invention. For example, coating solutions containing as little as 0.125% cellulose acetate phthalate by weight have been found sufficient to impart a slow timed-release characteristic to aspirin. Because of the cost of cellulose acetate phthalate, an upper practical limit of the cellulose acetate phthalate concentration in the coating solution generally is about 20% by weight, although higher concentrations can be used if desired. The preferred concentration of cellulose acetate phthalate in the coating solution is in the range of about 5 to about 18 percent by weight with a concentration of about 15 percent by weight being the most preferred. The coating solution can also include conventional pharmaceutically acceptable (i.e., safe for human consumption) plasticizers, such as diethylphthalate, to improve the flexibility of the resultant tablets and minimize their tendency to break up during handling. Representative examples of other conventional plasticizers includes those disclosed in the Hotko et al. U.S. Pat. No. 3,325,365 and the Gaunt U.S. Pat. No. 3,449,489. That is, esters of carboxilic acid, such as lower alkyl citrates, e.g., triethyl citrate and the like; acetyltributyl citrate; acethyltriethyl citrate; other phthalate esters, such as dimethyl phthalate; and other esters, such as benzyl benzoate.

The coating solution can be applied either to the particles of aspirin before tabletting or to the outer surface of tablets formed from ordinary aspirin containing conventional tabletting excipients, such as starch. When applied to preformed tablets of uncoated aspirin, the coating solution is applied directly to the outer surface of the tablet without any previous coatings, such as gelatin, natural gums, calcium sulfate or the like, typically used in enteric coating processes.

The coating solution is applied to the aspirin particles or aspirin tablet in any convenient manner capable of providing a continuous thin film of the cellulose acetate phthalate solution over the particles or tablet. When coating aspirin particles, the coating solution can be conveniently applied by spraying, dipping, ladling while the particles are being tumbled in a conventional apparatus or the like. Presently, the preferred method of coating the aspirin particles is to granulate standard size aspirin in the presence of a sufficient amount of the coating solution to completely coat each of the individual particles with a thin film of the solution. Since ordinary aspirin is typically granulated before being formed into a tablet, application of the coating solution in this manner does not require a separate coating step and production costs are minimized. In order to obtain the best results, the coating solution is slowly introduced into the granulating equipment while the aspirin particles are being granulated, e.g., over a 1 to 5 minute period, and the granulation is continued for a few additional minutes after all the coating solution has been added, e.g., 3 to 10 minutes, to insure each particle is coated with a thin film of the solution.

Although the release time can be varied by varying the size of the aspirin particles, it does not appear that particle size of the aspirin before and after granulation is particularly critical for obtaining the improved timed-release characteristics. Of course, particle sizes which are convenient for granulating and forming the granules into dosage-size tablets should be used. For example, it has been found that standard 80 mesh U.S.P. aspirin granulated into 20 mesh or larger granules works very satisfactorily. The release time is increased as the size of the aspirin particle is reduced because of the larger total surface area of coating per mass which must be eroded away by the intestinal fluids. The thickness of the resultant coating on the aspirin particles is primarily dependent upon the quantity of coating solution used during granulation, the concentration of cellulose acetate phthlate in the coating solution and the total granulating time. The thickness of the coating is generally increased, thus the release time increased, as these variables are increased. Therefore, these variables are adjusted to obtain a coating thickness which produces the desired timed-release characteristics. Typically, the amount of cellulose acetate phthalate applied to the aspirin particles, after removal of the solvent by drying, will be in the range of about 0.5 to about 5.0% by weight based on the total weight of the coated granules.

After applying the coating solution, the aspirin granules are dried. During the drying step, the granules are subjected to a temperature sufficient to evaporate substantially all of the solvent, thereby leaving a continuous coating of cellulose acetate phthalate over the granules. Following the drying step, the coated granules are treated in a conventional manner for forming a tablet, e.g., ground into convenient size for tabletting, mixed to homogenize the batch and formed into appropriate dosage-size tablets, (e.g., 10 grains) in a tablet press.

When the coating solution is applied to preformed tablets of untreated aspirin, the coating solution can be applied by spraying, dipping, ladling onto the tablets while they are being tumbled in a conventional apparatus and the like. From test results, it appears that the cellulose acetate phthalate is at least partially absorbed into the tablet and protectively coats the individual particles thereof. It has been found that the release pattern of the tablets so treated is substantially the same as that for tablet formed from coated aspirin particles. Where a slower release rate is desired, two or more coatings can be applied, with an intermediate drying step, to obtain a thicker resultant coating. Since coating tablets in this manner does require a separate coating step, with the attendant additional time and cost therefor, this method has less practical advantages from a production cost standpoint than granulating the aspirin particles in the presence of the coating solution before tabletting.

For some purposes, it may be desirable for an aspirin tablet to provide both immediate pain relief and sustained pain relief. This capability can be provided by forming a double-layered tablet, one layer being formed from aspirin particles containing conventional tabletting excipients and the other layer being formed from particles of aspirin coated in accordance with this invention. The separate layers of particles are introduced into a conventional two layer tablet press where they are pressed into a single double-layered tablet. The quantity of aspirin in each layer is varied depending upon the desired dosage for each type of pain relief. For example, a double-layered tablet having a total dosage of 10 grains can be produced with 6 grains being coated, dosage of 10 grains can be produced with 6 grains being coated, timed-released aspirin and 4 grains being ordinary aspirin. When a double-layered tablet prepared in this manner is ingested, the layer of ordinary, uncoated aspirin dissolves immediately in the stomach to provide immediate relief. The layer of coated aspirin remains in tact while in the stomach and dissolves at a slow, controlled rate in the intestinal tract to maintain a level of pain relief for a sustained period of time. When preformed tablets of untreated aspirin are coated with the coating solution in accordance with one embodiment of this invention, it cannot be made into a double-layer tablet because of the inability of the layer of uncoated aspirin to adequately adhere to the coated tablet. Therefore, aspirin tablets should be coated previously to tabletting an pressed into a tablet along with the ordinary aspirin when a double-layered tablet is to be made.

EXAMPLE I

A representative coating solution is made according to the following formulation:

| Ingredient | Quantity, $k_g$ |
|---|---|
| Cellulose acetate phthalate | 6 |
| Methylene chloride | 17 |
| Diethylphthalate | 1.2 |
| Acetone | 15 |

The cellulose acetate phthalate is first added to the acetone and mixed to obtain complete dissolution. The diethylphthalate is added to the solution while mixing and the methylene chloride is then added to obtain the coating solution.

65kg of 80 mesh aspirin U.S.P. are placed in a Hobart mixer and, while mixing 2 gallons of the above coating solution are introduced into the mixture over a period of 2 minutes. After addition of the coating solution, mixing is continued for an additional 4 minutes (6 minutes total mixing) to insure that the individual particles of the aspirin and the resultant granules are completely coated with a thin film of the solution. The thus-coated aspirin granules are transferred to paper-lined oven trays, dried in ambient air for 1 hour and then subsequently dried in an oven 125° F for 1½ hours. The dried granules, containing approximately 0.76 to 0.91% cellulose acetate phthalate by weight, are then removed from the oven and are allowed to cool at room temperature for 30 minutes. The cooled granules are then introduced into a Fitzmill grinder in which they are ground into a smaller size and forced through a 20 mesh screen. The granules are mixed in a Hobart mixer for about 2 minutes to homogenize the batch. The total weight of the granules is approximately 65.8 kg. The coated aspirin granules are then pressed into dosage-sized tablets (e.g., 10 grains) in a conventional tabletting press.

EXAMPLES II

A double-layer aspirin tablet having one layer of timed-released aspirin and one layer of standard aspirin are pressed in a conventional two layer press. The timed-release layer consists of 6 grains of aspirin granules prepared in accordance with the procedure outlined in Example I and the other layer consists of 4 grains of standard 80 mesh aspirin admixed with starch as a tabletting excipient, the amount of starch being approximately 10% by weight of the admixture.

EXAMPLE III

A double-layered tablet prepared in accordance with the procedure outlined in Example II was subjected to standard U.S.P. in vitro disintegration tests using simulated gastric juice and intestinal fluid. The layer of standard aspirin was completely dissolved in the gastric juice within 45 seconds and approximately 5.6 weight percent of the timed-released layer dissolved in the gastric juice after 1 hour. The dissolution of the timed-released layer in the intestinal fluid is summarized in Tablet I below.

TABLE I

| Total Time in Intestinal Fluid (after 1 hour in gastric juice), Hours | Cumulative Wt. % Timed-Release Layer Dissolved |
|---|---|
| 1 | 53.3 |
| 2 | 80.5 |
| 3 | 94.9 |
| 4.6 | 100 |

From these test results it can be seen that there is minimal dissolution of the timed-released layer in the simulated gastric juice while there is a complete dissolution thereof in the simulated intestinal fluid at a very slow rate.

Aspirin tablets containing about 10% starch by weight have been coated with the coating solution described in Example II by ladling the solution on while the tablets were being tumbled. In vitro tests of tablets coated in this manner produced results substantially the same as those described above for tablets formed from coated aspirin particles.

EXAMPLES IV

In vivo tests were performed with a 10 grain aspirin tablet prepared in accordance with the procedure outlined in Example I (designated A below), a double-layered combination 10 grain tablet prepared in accordance with the procedure outlined in Example II (designated B below) and a commercially avabilable timed-release 10 grain aspirin tablet prepared by an ethyl cellulose micro-encapsulation procedure (designated C below) to evaluate their biological availability. The tablets were ingested on different days by a 42 year old male, 5 feet 8 inch tall and weighing 168 pounds. Blood samples were taken at various intervals and analyzed for aspirin content. The results of these tests are tabulated in the Table II below and graphically illustrated in FIG. 1.

TABLE II

| Time After Ingestion, Hours | Blood level, mg/100ml plasma | | |
|---|---|---|---|
| | A | B | C |
| .5 | 0.11 | 0.59 | 0.30 |
| 1.5 | 0.36 | 1.60 | 0.15 |
| 4 | 0.37 | 1.60 | 3.54 |
| 6 | 0.35 | 1.28 | 3.20 |
| 8 | 0.31 | 0.95 | 2.06 |
| 12 | 0.27 | 0.52 | 0.97 |
| 18 | 0.18 | 0.33 | 0.19 |
| 24 | 0.20 | 0.33 | <0.05 |
| 30 | 0.17 | — | — |
| 36 | 0.24 | — | — |
| 48 | 0.18 | <0.05 | — |

From these test results it can be seen that a 10 grain timed-release aspirin tablet prepared in accordance with this invention provides a relatively constant, low blood level for up to 48 hours, as contrasted to the commercially available timed-release tablet which produces an initially high blood level content with a rapidly decreasing content. Also, it can be seen that a double-layered 10 grain aspirin tablet, including a layer of standard aspirin, prepared in accordance with this invention, produces a more rapid release of aspirin but at a lower initial peak and the blood level decreases more gradually than that provided by the commerically available timed-release aspirin tablet. Therefore, larger initial doses can be taken of either a purely timed-released aspirin tablet or a double-layered tablet prepared in accordance with this invention to obtain a more constant pain relief for a longer period, without an initially high blood level peak resulting in potential toxicity and/or other harmful side effects.

EXAMPLE V

Figure 2:
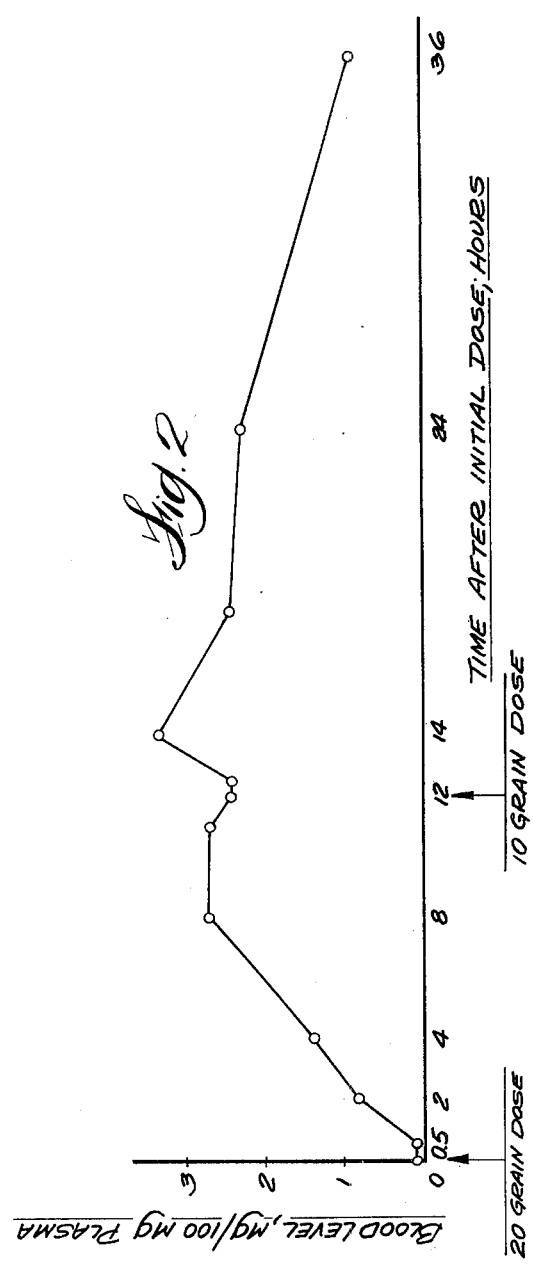
FIG. 2 is a graphical illustration of the results of the test described in Example VI showing the blood level profile when successive doses of timed-release aspirin produced in accordance with this invention are taken.

An in vivo test was conducted to evaluate the biological availability of an aspirin tablet prepared in accordance with this invention. Two double-layered 10 grain aspirin tablets prepared in accordance with the procedure outlined in Example II were initially ingested by the same man as described in Example IV and 12 hours after the taking of the first dose a single double-layered 10 grain tablet prepared in the same manner was ingested. Blood samples were taken at various intervals and analyzed for aspirin content. The results of this test are tabulated in Table III below and graphically illustrated in FIG. 2.

TABLE III

| Time After Initial Dosage, Hours | Blood level, mg/100 ml plasma |
|---|---|
| 0 | <0.05 |
| .5 | <0.05 |
| 2 | 0.89 |
| 4 | 1.50 |
| 8 | 2.85 |
| 11 | 2.85 |
| 12 (Additional 10 grain dose) | 2.51 |
| 12.5 | 2.51 |
| 14 | 3.52 |
| 18 | 2.60 |
| 24 | 2.45 |
| 36 | 0.94 |

From these test results, it can be seen that a substantially constant blood level existed for a period spanning from eight hours after the initial dosage to 24 hours after the initial dosage when a second dosage was taken 12 hours after the initial dosage. The layer of standard aspirin ordinarily dissolves in the stomach within a manner of minutes and is reflected in the blood level. Therefore, it is believed that the lower level blood content of the particular patient tested during the first 8 hours following the initial dosage was caused by specific physiological factors of the patient at the time of initial ingestion and the data is not representative of the effectiveness of the aspirin during this period. This is borne out by the test described in Example IV where the same man ingested a double-layer tablet and there was a reflection of aspirin content in the blood within a relatively short time. The important effect shown by this test is the maintenance of a substantially constant blood level content for a long period of time, (i.e., up to 24 hours or more) without a significant peak in the blood level upon the ingestion of a second dosage. This means that long term constant pain relief can be obtained by taking successive dosages at prescribed intervals without the danger of blood level peaks where toxicity or harmful side effects might occur.

As will be readily apparent to those skilled in the art upon reading the above detailed description, various modifications can be made thereto without departing from the spirit and scope of the invention.

We claim:

1. A method for making a multi-layer aspirin tablet including at least one layer having timed-release characteristics comprising:
   a. mixing uncoated particles of standard 80 mesh U.S.P. aspirin with a non-aqueous solution comprised of about 5 to about 18 weight % cellulose acetate phthalate, a pharmaceutically acceptable plasticizer and a pharmaceutically acceptable solvent, the amount of said solution being sufficient to coat and impregnate each of the particles with said solution;
   b. forming the resultant mixture into discrete granules;
   c. drying said granules to remove substantially all of said solvent therefrom;
   d. reducing the resultant granules to a size whereby they can pass through a 20 mesh screen;
   e. homogenizing said reduced granules by mixing;
   f. forming a first layer of said reduced granules containing no tabletting excipients;
   g. forming a second layer of standard U.S.P. aspirin particles adjacent said first layer; and
   h. compressing said layers together in a tabletting press to form said multi-layer aspirin tablet.

2. A method according to claim 1 wherein the amount of cellulose acetate phthalate in said solution is about 15 weight %.

3. A method according to claim 1 wherein said solvent is selected from the group consisting of acetone, methyl ethyl ketone, methanol, ethanol, isopropanol, methylene chloride, ethylene dichloride, chloroform and mixtures thereof.

4. A method according to claim 3 wherein said plasticizer is diethyl phthalate.

5. A method according to claim 4 wherein the amount of said diethyl phthalate in said solution is about 3 weight %.

6. A method according to claim 3 wherein the amount of said cellulose acetate phthalate contained in each of said granules after drying is about 0.5 to about 5.0 % by weight, based on the total weight of said granule.

7. A multi-layer aspirin tablet produced by the process of claim 1.

* * * * *